US00PP33111P2

(12) United States Plant Patent
Wheeler et al.

(10) Patent No.: US PP33,111 P2
(45) Date of Patent: Jun. 1, 2021

(54) BLUEBERRY PLANT NAMED 'BB15-214PO-3'

(50) Latin Name: *Vaccinium corymbosum*
Varietal Denomination: BB15-214PO-3

(71) Applicant: Berry Blue, LLC, Grand Junction, MI (US)

(72) Inventors: Edmund J. Wheeler, Holland, MI (US); James F. Hancock, Scarborough, ME (US); Maria Pilar Banados, Santiago (CL)

(73) Assignee: Berry Blue, LLC, Grand Junction, MI (US)

( * ) Notice: Subject to any disclaimer, the term of this patent is extended or adjusted under 35 U.S.C. 154(b) by 0 days.

(21) Appl. No.: 16/993,057

(22) Filed: Aug. 13, 2020

(51) Int. Cl.
*A01H 6/36* (2018.01)
*A01H 5/08* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — King IP Law; Joshua King

(57) ABSTRACT

'BB15-214PO-3', is the first known genotype selected in a tropical environment of Peru. 'BB15-214PO-3' does not require chill-hours for either budbreak or fruit production, since it does not develop endo-dormancy. The fruit of 'BB15-214PO-3' is a medium size berry, with medium blue color, with excellent fruit firmness and very juicy and crunchy texture. The eating quality of 'BB15-214PO-3' is excellent a superior to many of the varieties currently grown in Peru, with a sugar/acidity balance of 40 to 50. Time of fruit production in 'BB15-214PO-3' can be regulated by the pruning date and environment conditions.

5 Drawing Sheets

Latin name: *Vaccinium corymbosum.*
Common name: Blueberry.
Cultivar name: 'BB15-214PO-3'.

BACKGROUND AND SUMMARY

Blueberries are a well-known fruit enjoyed by many throughout the world. The novel blueberry variety in this application, 'BB15-214PO-3', is the first genotype from Berry Blue Genetics selected in a tropical environment of Peru.

One example of an existing known blueberry variety is 'Ventura', U.S. Plant Pat. No. 24,606. Compared to 'Ventura', 'BB15-214PO-3' has lower vigor and smaller plant size. The fruit of 'BB15-214PO-3' is well presented on the plant and is produced in current season shoots rather than in 1-year-old shoots, which is another particular feature of 'BB15-214PO-3'. The fruit of 'BB15-214PO-3' is juicy, with excellent flavor and firmness, and it has a good balance of sweetness and acidity.

Comparing 'BB15-214PO-3' to 'Stellar' (brand name for "BB06-50FL-1", U.S. Plant Pat. No. 30,445), the immature summer cane color of BB15-214PO-3' is yellow green, compared to olive green; the fruit of 'BB15-214PO-3' is slightly smaller in size and more flat compare to 'Stellar'; and the mature leaves of 'BB15-214PO-3' are shorter and less wide than the mature leaves of 'Stellar'.

Additional examples of an existing, patented blueberry variety are 'Rocio', U.S. Plant Pat. No. 20,374, 'Kestrel' (brand name for FL02-40, U.S. Plant Pat. No. 21,719) and Presto (brand name for 'BB07-7FL-4', U.S. Plant Pat. No. 30,421). Compared with these varieties in Peru, the acidity of 'BB15-214PO-3' is much lower as shown in Table 1, which provides fruit characteristics of 'BB15-214PO-3' compared to several other commercial varieties grown in Peru.

| Location | Cultivar | Firmness/ Baxlo (shore) | Sugar Content (°brix) | Acidity (%) | Ratio °Brix/ Acidity |
|---|---|---|---|---|---|
| Chao, Peru | Ventura | 78 | 13.3 | 1.10 | 12.1 |
| Olmos, Peru | Rocío | 74 | 11.0 | 0.90 | 12.2 |
| Chao, Peru | Stellar | 78 | 12.0 | 0.72 | 16.6 |
| Olmos, Peru 2018 | Presto | 74 | 13.4 | 0.68 | 19.7 |
| Olmos, Peru 2018 | BB15-214PO-3 | 81 | 15.0 | 0.34 | 44.1 |

The present cultivar, 'BB15-214PO-3', provides one or more advantages compared to these and/or other blueberry varieties.

The fruit of 'BB15-214PO-3' is medium blue color, with excellent firmness and very juicy and crunchy texture. The eating quality of 'BB15-214PO-3' is excellent, having a sugar/acidity balance of 40 to 50, apparently better than any other commercial cultivar in Peru. 'BB15-214PO-3' is a highly productive variety with early maturity fruit and very good fresh market quality and storage ability. Time of fruit production in 'BB15-214PO-3' can be regulated by the pruning date and environment conditions. This is another distinct characteristic of 'BB15-214PO-3', particularly in this new tropical environment for blueberries. 'BB15-214PO-3' does not require chill-hours for either budbreak or fruit production, which appears to be because 'BB15-214PO-3' does not develop endo-dormancy. 'BB15-214PO-3' was selected in sandy soil and tested also under substrate soilless production.

Areas of adaptation of 'BB15-214PO-3' include coast of Perú, Ecuador, and Colombia and other tropical areas with no chill conditions. 'BB15-214PO-3' has not yet been tested in temperate zone areas.

Plants of 'BB15-214PO-3' are medium upright with a medium size crown 'BB15-214PO-3' produces many upright canes, with good leafing and flowering.

The fruit of 'BB15-214PO-3' are sweet with low acid, have a firm and crunchy berry adapted to a tropical non-chill environment. The berry scar of 'BB15-214PO-3' is small and dry. 'BB15-214PO-3' shows long fruit storability of about 5 to 6 weeks. The productivity of 'BB15-214PO-3' is similar to 'Kestrel' or 'Presto' in Peru, although it has yet not been tested commercially.

The flowering period of 'BB15-214PO-3' is similar to 'Kestrel' or 'Rocio' in the same tropical environment of Peru. Flowering of 'BB15-214PO-3' starts 80 to 85 days after pruning, which is shorter than 'Scintilla' (U.S. Plant Pat. No. 19,233) and 'Ventura', which take about 120 to 150 days. The fruiting period of 'BB15-214PO-3' is similar to 'Kestrel', 'Presto' and 'Rocio', starting about 133 to 146 days after pruning and lasting for 5 to 6 months. Ripening of 'BB15-214PO-3' is extended and it keeps a uniform berry size during the season. 'BB15-214PO-3' appears to be the first true Tropical Highbush blueberry variety.

BRIEF DESCRIPTION OF THE PHOTOGRAPHS

DETAILED DESCRIPTION

Figure 1B:
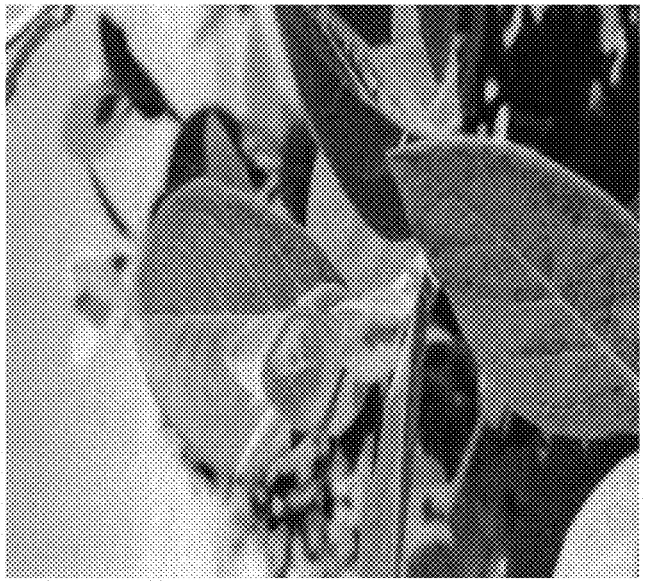
FIGS. 1A and 1B are close-up photographs of 'BB15-214PO-3' taken February 2020, Chao, Peru, and showing the leaf color, shape, venation, and petioles.
Figure 1A:
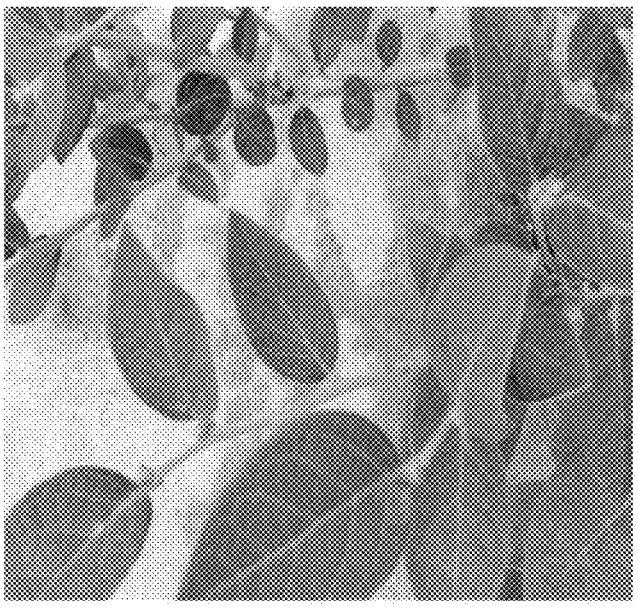
Figure 2B:
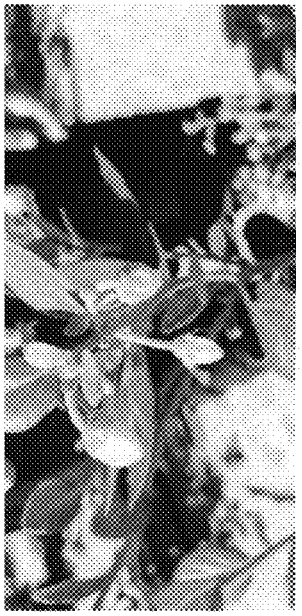
FIGS. 2A, 2B and 2C are close-up photographs taken May 2020, in Chao, Peru, showing the color and shape of open and un-opened flowers, and the shape and color of flower buds, of a 5-year-old bush of 'BB15-214PO-3'
Figure 2C:
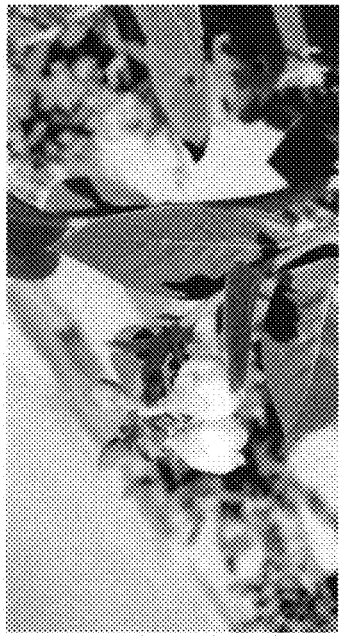
Figure 2A:
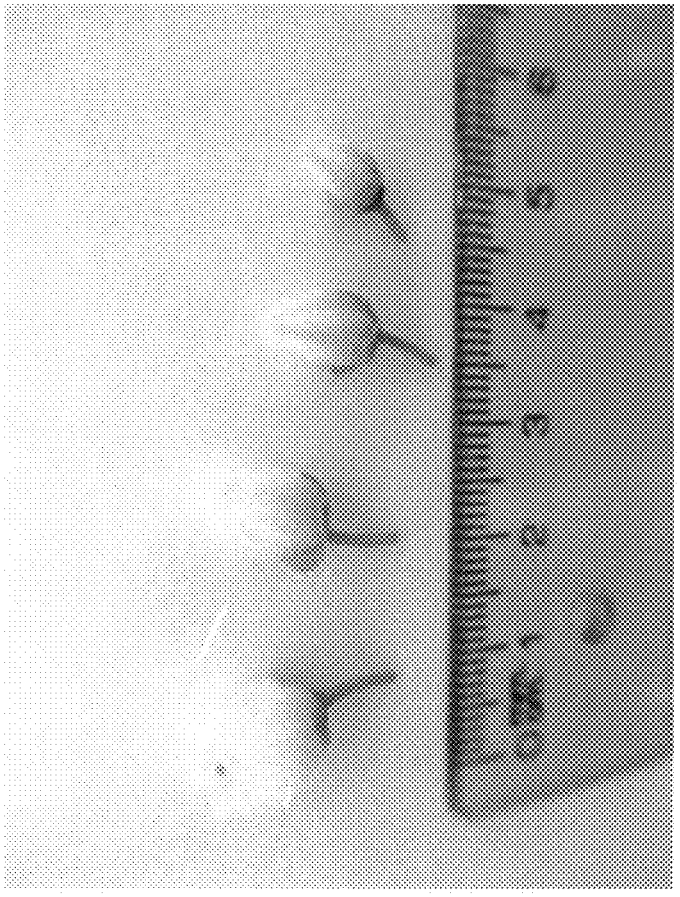
Figure 3B:
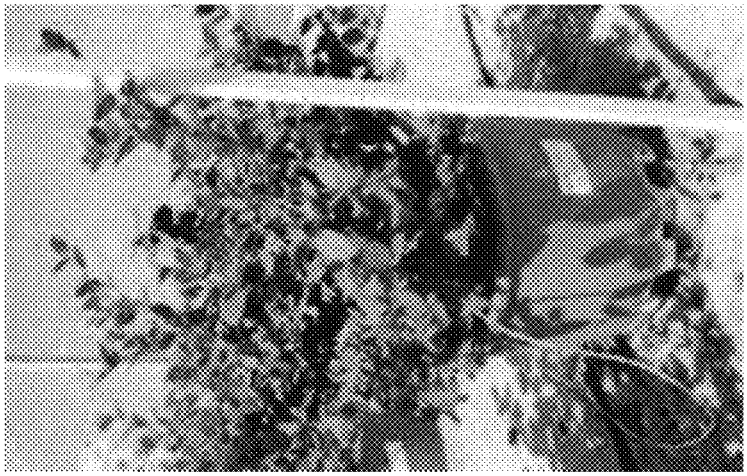
FIGS. 3A and 3B are photographs of 'BB15-214PO-3' grown in a pot and taken May 2020, Chao, Peru, showing the overall bush shape, leaf color, color and structure of mature canes, the presentation of the fruit and cluster density, size and color of ripe and unripe fruit and overall yield.
Figure 3A:
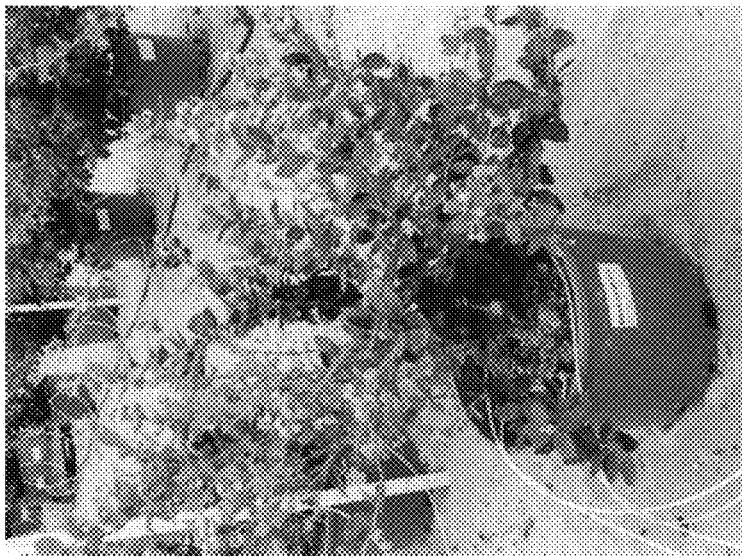
Figure 4B:
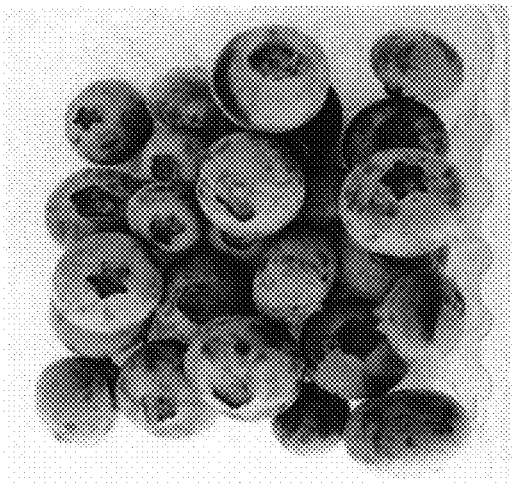
FIGS. 4A and 4B are close-up photographs of 'BB15-214PO-3' taken February 2020, Chao, Peru, and showing the size, shape, and color of ripe fruit.
Figure 4A:
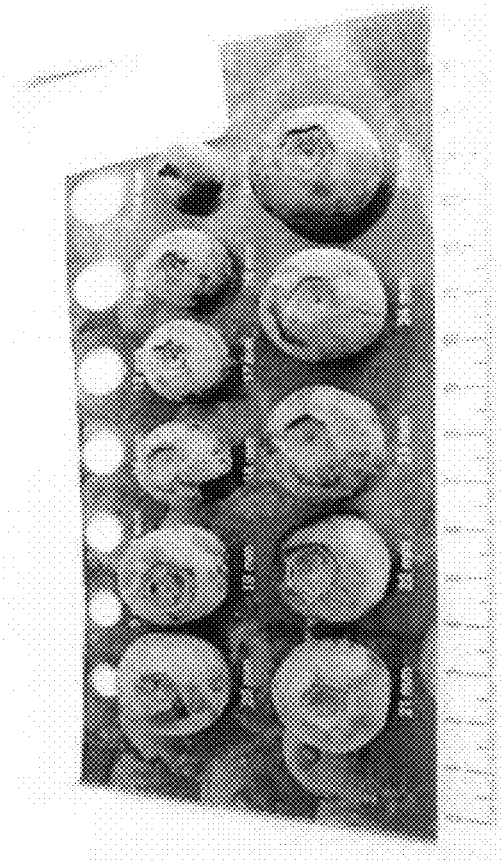
Figure 5B:
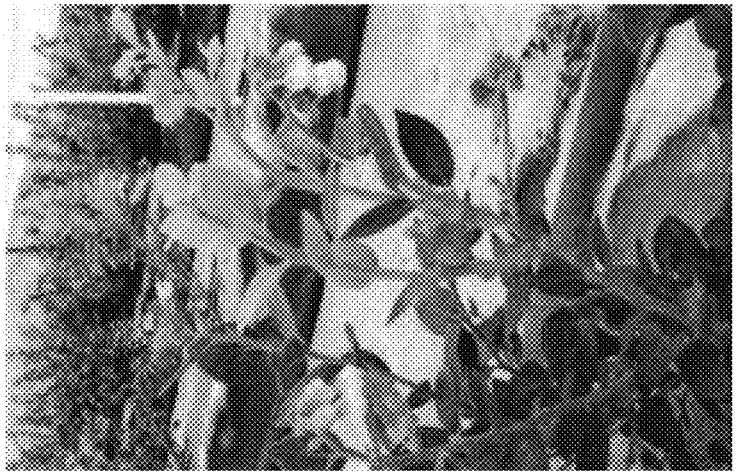
FIGS. 5A and 5B are close-up photographs of 'BB15-214PO-3' taken February 2020, Chao, Peru, and showing the plant with flowers and a fruiting lateral 'BB15-214PO-3'.
Figure 5A:
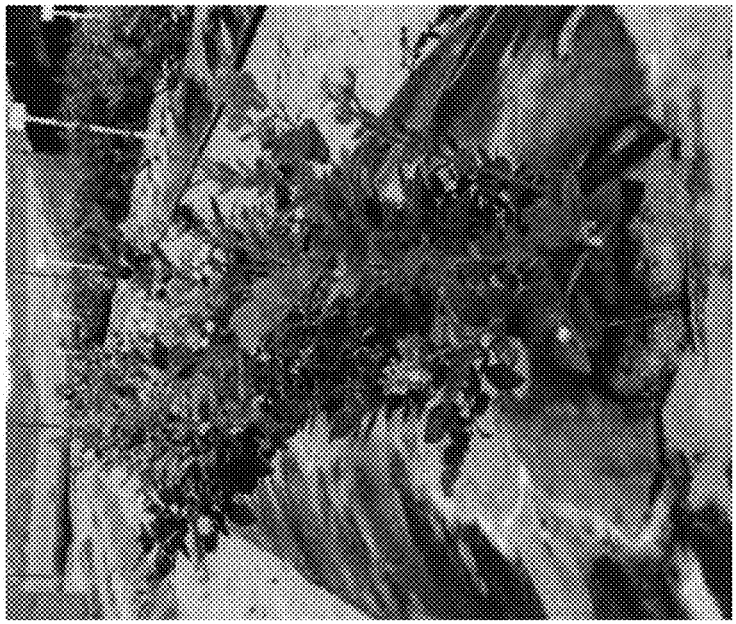

Note: statements of characteristics herein represent exemplary observations of the cultivar performance in Olmos, Peru 6°5'27"S 79°56'6"W and Chao, Peru 8°35'12"S 78°35'58"W and will vary depending on time of year, location, annual temperature conditions and weather, etc. Where dimensions, sizes, colors, and other characteristics are given, it is to be understood that such characteristics are approximations and averages. The descriptions reported herein are based on the original selected individual bush observed in successive years through 2017, 2018, 2019, and 2020 in fields near Olmos, Peru and Chao, Peru and also in cloned plants planted in Chao, Peru in 2019 and 2020. Laboratory analysis of fruit characteristics were done in Olmos, Peru and Chao, Peru.

Cultivar name: 'BB15-214PO-3'.

Classification:

*Family*.—Ericaceae.

*Botanical name*.—*Vaccinium corymbosum*.

*Common name*.—Blueberry.

Parentage:

*Female parent*. Name: 'BB07-249GA-3' (brand name, 'Candy Crunch'; child of 'Gupton' (unpatented) x Sweetcrisp' (U.S. Plant Pat. No. 20,027)). USPP: Unpatented; application filed with U.S. Patent and Trademark Office Dec. 31, 2019. Compared to 'BB07-249GA-3', 'BB15-214PO-3' produces fruit on current season shoots, and 'BB07-249GA-3' has larger fruit size and higher sugar content and is less acidic. 'BB07-249GA-3' has not been tested yet in the same environment as 'BB15-214PO-3'.

*Male parent*.—Name: 'BB06-538MX-2' (child of 'Sapphire' (U.S. Plant Pat. No. 11,829) and 'Palmetto' (U.S. Plant Pat. No. 16,756). United States Plant Patent: Unpatented. Compared to 'BB06-538MX-2', fruit of 'BB15-214PO-3' is larger and firmer. They both produce fruit on current season shoots. 'BB15-214PO-3' originated as a seedling selected from a cross of 'Candy Crunch' and 'BB06-538MX-2' made in a greenhouse in Grand Junction, Mich. in 2015. Seed was germinated in Chile and plants of that cross were grown and then sent and planted in a seedling evaluation site in Olmos, Province of Lambayeque, Peru for two years. The plant was first selected in November 2017 based on its excellent fruit characteristics both in the field and after 5 days cold storage and was given the number 'BB15-214PO-3'. It was tested under this number for two years. The individual bush was observed and evaluated for productivity and fruit quality in the same site for two successive years through 2019. An additional 3 bushes were propagated by vegetative cuttings and planted in an advanced trial in a soilless system near Chao, Peru in 2018 and the fruit was evaluated. All of the observed bushes have retained the characteristics of the original selection. 'BB15-214PO-3' has been asexually propagated via tissue-cultured microshoots since 2019 and multiplied and rooted in Chao, Peru. Propagated plants have been under evaluation since October 2019. General description of 'BB15-214PO-3'. 'BB15-214PO-3' is a new and distinct non-chill tetraploid Southern/Tropical highbush blueberry variety (*Vaccinium*) of complex ancestry, based largely on *V. corymbosum* and *V. darrowii,* from the breeding program of Berry Blue, LLC. 'BB15-214PO-3' is a very productive early-season variety with high quality fresh market characteristics 'BB15-214PO-3' is particularly well suited to be cultivated in tropical areas. 'BB15-214PO-3' has a good upright bush and a medium sized crown with many new canes. The bush has a very good vigor. It has shown very good adaptability to sandy soil and substrate mix of coco fiber and peat. The fruit itself is medium blue color, with excellent firmness and very juicy and crunchy texture. The eating quality is excellent with a sugar/acidity balance better than any other commercial cultivar in Peru. Fruit should be picked on a regular schedule about 4 to 7 days to maintain the quality of the fruit. 'BB15-214PO-3' will be released as the first cultivar selected in Perú and it is an improvement over 'Rocio' and "Kestrel' in terms of flavor. References to color refer to The Royal Horticultural Society Colour Chart 2007 Fifth Edition. Morphological characteristics reference: Plant Systematics, Jones and Luchsinger, 2 Ed., McGraw Hill, New York, ISBN 0-07-032796-3, 1986. Device used to measure Soluble Solids (SS-Brix°), Titratable acidity (TA), pH: PAL-BX/Acid 7, Atago USA, Inc., Bellevue, Wash. Firmness readings: Shore by BAXLO Durometer (Olmos, Peru). Sugar and acidity measurements, ATAGO (Olmos, Peru). General Description: medium upright with a medium size crown; sweet, low acid, firm and crunchy berry adapted to a tropical non-chill environment. 'BB15-214PO-3' blooms about 80 to 85 days after pruning. The average 50% ripening date is 250 days after pruning. Firmness ranges from 70 to 84 Baxlo Shore, Brix° from 14 to 15% and titratable acidity from 0.3 to 0.45% (Table 1) and a sugar to acid ratio of 40 to 50. Storability is long and it could last up to 30 days or more in cold storage.

Specific features of the variety:

Plant:

*Growth habit*.—Medium upright.
*Plant width*.—90 cm at mid-bush height.
*Plant height*.—100 cm.
*Productivity*.—1.5 kg per plant.
*Cold hardiness/tolerance*.—Not tested and not applicable to a tropical environment.
*Chilling requirement*.—This is a tropical highbush and this plant does not require chill hours for bud break.
*Canes*.—Moderately branched, average 5 to 6 shoots per bush, average 70-80 cm length, medium number of laterals.
*Young current-season-shoots*.—Yellow-Green Group 144A.
*One-year-old shoot branches color*.—Yellow-Green Group 144C. Texture is soft.
*Mature cane color*.—Yellow green group N144A.
*Mature cane texture*.—Medium rough.
*Fruiting wood current season shoots*.—
*Internode length range*.—4 to 5 cm.
*Surface texture of new wood*.—Smooth.
*Time of beginning of leaf bud burst*.—Bud break occurs 7 to 10 days after pruning.
*Time of beginning of flowering*.—60 to 70 days after planting or pruning in Chao, Peru.
*Date of* 50% *open flowers*.—75 to 85 days after planting or pruning in Chao, Peru.
*Time of beginning of fruit ripening*.—Fruit ripening begins on August 20 but is dependent on the pruning time.
*Disease resistance/susceptibility*.—None claimed.
*Young current-season-shoots*.—Yellow-Green Group 144C.
*One-year-old short branches color*.—Yellow-Green Group 144C. Texture is soft.

Foliage:

*Young, newly expanded leaf color*.—Upper surface: Yellow-Green Group 146A; Lower surface: Green Group 139D.
*Leaf arrangement*.—Simple Alternate.
*Mature, fully expanded leaves*.—Upper surface: Green 138A; Lower surface: Green 138B.
*Leaf margins*.—Entire.
*Leaf venation*.—Pinnate.
*Leaf shape*.—Medium obtuse.
*Leaf length*.—66 mm to 70 mm, average 68 mm.
*Leaf width*.—32 mm to 42 mm, average 36 mm.
*Leaf color*.—Yellow-Green Group 144 AB.
*Leaf apices*.—Acuminate.
*Leaf bases*.—Acute.
*Vein and petiole coloration*.—Yellow-Green Group, 144 A and 144 B.
*Petiole length*.—5 mm.
*Petiole diameter*.—5.59 mm.
*Evergreen*.—This variety is evergreen and keep its leaves during the entire year.
*Fall leaf color*.—Does not apply for this genotype.

Leaf dimensions:

*Overall shape*.—Medium Obtuse.
*Length*.—66 to 70 mm, Average 68 mm.
*Width*.—32 to 42 mm, Average 36 mm.
*Leaf margins*.—Entire, no visible (microscope 10X) pubescence and a few nectaries.
*Leaf surface*.—Smooth upper and lower, no visible (microscope 10X) pubescence.

Leaf buds:

*Shape*.—Medium obtuse.
*Length*.—1 to 2 mm.
*Width*.—1 mm.
*Color*.—Yellow Green Group 144AB.

Flower buds:

*Shape*.—Round.
*Length*.—8.18 mm.
*Width*.—5.54 mm.
*Color*.—White group 155B.

Flower:

*Flower shape*.—Medium urceolate.
*Flower bud number per lateral*.—6 to 8.
*Flowers per bud*.—5 to 7.
*Flower fragrance*.—Light floral.
*Corolla color*.—White Group 155B.
*Corolla length*.—7.13 mm.
*Corolla width*.—5.5 mm.
*Corolla aperture width*.—3.5 mm.
*Corolla texture*.—Smooth.
*Flower peduncle length*.—9 mm.
*Peduncle diameter*.—0.5 mm.
*Peduncle texture*.—Smooth.
*Peduncle color*.—Green Group 143A.
*Flower pedicel length*.—9 mm.
*Pedicel diameter*.—9 mm.
*Pedicel texture*.—Smooth.
*Pedicel color*.—Green Group 143 A.
*Calyx* (*with sepals*).—3 mm.
*Calyx color*.—Green Group 143 B.
*Stamen length*.—5 to 6 mm.
*Stamen number per flower*.—10.
*Stamen filament color*.—Greyed Orange Group 163A.
*Style*.—5.4 mm, top of ovary to stigma tip.
*Style color*.—Green group 143A.
*Pistil extends over the top of corolla*.—1 mm.
*Ovary color*.—Medium Green 145A.
*Anther length*.—4.2 mm.
*Number*.—1.
*Anther color*.—Greyed-Orange group 163A.

Pollen:

*Abundance*.—Medium high.
*Color*.—Yellow 10D.

Fruit:

*Date of* 50% *maturity*.—200 to 230 days after pruning.

*Duration of ripening*.—Average 65 to 80 days from bloom to ripen in Olmos, Peru and Chao, Peru. Ripening period can last 6 months.

*Yield*.—1.5 kg per plant.

*Cluster density*.—Loose.

*Immature fruit color*.—Yellow Green Group N 144C.

*Berry color with wax*.—Blue Group 100 B.

*Berry color with wax removed*.—Blue Group 103A.

*Berry flesh color*.—Yellow Green Group 149B and D.

*Berry surface wax abundance*.—Heavy, persistent.

*Berry weight*.—3.4 grams/berry.

*Berry size diameter*.—20.8 mm.

*Berry height*.—12.8 mm.

*Berry width*.—20.8 mm.

*Aspect* (*H/W*).—0.61.

*Berry shape*.—Oblate.

*Average number of fruits per cluster*.—This genotype does not produce in cluster.

*Detachment force*.—Easy.

*Self-fruitfulness*.—Fair, cross pollination may be desirable for maximum yield and fruit size.

*Fruit stem scar*.—1 mm diameter, 1 mm depth.

*Calyx*.—5 point.

*Calyx diameter*.—4.21 mm.

*Calyx depth*.—2.20 mm.

*Berry firmness*.—Firm, 75 to 84 Shore of Baxlo.

*Berry sweetness*.—High, Brix°=14 to 15.

*Berry acidity*.—Titratable acidity=0.35% to 0.45%.

*Berry flavor and texture*.—Good blueberry flavor, balanced sugar and acidity, juicy and crunchy texture.

*Storage ability*.—Medium high, 3-4 weeks in refrigerated storage.

*Suitability for mechanical harvesting*.—Not tested.

Seed:

*Seed abundance in fruit*.—Medium, 10-15 seed per fruit.

*Seed color*.—Grey orange group 165B.

*Seed dry weight*.—8 mg.

*Seed size*.—1.2 mm length, 0.6 mm width.

Possible typical market uses: Mainly fresh market. It can also be used for processing and/or as frozen fruit.

What is claimed is:

1. A new tropical highbush blueberry plant cultivar named 'BB15-214PO-3' as described and shown herein.

* * * * *